United States Patent
Roberts

(10) Patent No.: US 7,233,015 B2
(45) Date of Patent: Jun. 19, 2007

(54) SYSTEM AND METHOD FOR DETECTING LIQUID FLOW FROM A NOZZLE IN A SEMICONDUCTOR PROCESSING DEVICE

(75) Inventor: Kenneth L. Roberts, Forney, TX (US)

(73) Assignee: Texas Instruments Incorporated, Dallas, TX (US)

( * ) Notice: Subject to any disclaimer, the term of this patent is extended or adjusted under 35 U.S.C. 154(b) by 179 days.

(21) Appl. No.: 10/983,007

(22) Filed: Nov. 4, 2004

(65) Prior Publication Data

US 2006/0091335 A1 May 4, 2006

(51) Int. Cl.
*B41J 29/393* (2006.01)

(52) U.S. Cl. .................. 250/573; 250/227.11; 340/603

(58) Field of Classification Search ........... 250/227.11, 250/573–576; 356/436; 137/487.5; 73/1.31, 73/1.74, 36, 293, 294, 861; 340/603, 606, 340/618, 619
See application file for complete search history.

(56) References Cited

U.S. PATENT DOCUMENTS

| | | |
|---|---|---|
| 6,189,565 B1 * | 2/2001 | Skog ........................... 137/554 |
| 6,641,246 B2 * | 11/2003 | Endo et al. .................... 347/19 |
| 2004/0112840 A1 * | 6/2004 | Bourazak et al. ........... 210/748 |

* cited by examiner

*Primary Examiner*—Georgia Epps
*Assistant Examiner*—Tony Ko
(74) *Attorney, Agent, or Firm*—Peter K. McLarty; W. James Brady, III; Frederick J. Telecky, Jr.

(57) ABSTRACT

A system for detecting liquid flow from a nozzle in a semiconductor processing device includes a first fiber optic sensor, a second fiber optic sensor, and an amp. The first fiber optic sensor and second fiber optic sensor are located on opposite sides of at least one nozzle. The first fiber optic sensor transmits light, and the second fiber optic sensor receives more of the light when the nozzle is not dispensing liquid than when the nozzle is dispensing liquid. The amp is coupled to the first fiber optic sensor and second fiber optic sensor. The amp indicates whether the nozzle is dispensing liquid according to an amount of the light received at the second fiber optic sensor.

10 Claims, 3 Drawing Sheets

SYSTEM AND METHOD FOR DETECTING LIQUID FLOW FROM A NOZZLE IN A SEMICONDUCTOR PROCESSING DEVICE

TECHNICAL FIELD OF THE INVENTION

This invention relates generally to the field of semiconductor processing and, more specifically, to a system and method for detecting liquid flow from a nozzle in a semiconductor processing device.

BACKGROUND OF THE INVENTION

During the production of semiconductor devices, manufacturing equipment uses nozzles to dispense liquid chemicals onto semiconductor wafers. The manufacturing equipment may include devices, such as suckback valves, to prevent the liquids from continuously dripping onto the deck of the semiconductor manufacturing equipment or on the wafer. In the event that the suckback valve or other equipment fails to prevent dripping, the wafers produced by the manufacturing equipment may include corrosion or other defects.

SUMMARY OF THE INVENTION

In accordance with the present invention, a system and method for detecting liquid flow from a nozzle in a semiconductor processing device is provided that substantially eliminates or reduces disadvantages or problems associated with previously developed systems and methods.

In one embodiment, a system for detecting liquid flow from a nozzle in a semiconductor processing device includes a first fiber optic sensor, a second fiber optic sensor, and an amp. The first fiber optic sensor and second fiber optic sensor are located on opposite sides of at least one nozzle. The first fiber optic sensor transmits light, and the second fiber optic sensor receives more of the light when the nozzle is not dispensing liquid than when the nozzle is dispensing liquid. The amp is coupled to the first fiber optic sensor and second fiber optic sensor. The amp indicates whether the nozzle is dispensing liquid according to an amount of the light received at the second fiber optic sensor.

The present invention provides a number of important technical advantages. The present invention may detect leaks or dripping that may occur from a nozzle in a semiconductor processing device. Compared to previous techniques, the present invention more quickly and more efficiently detects problems so that they can be corrected before the problem results in the defect of numerous wafers. For these and other readily apparent reasons, the present invention represents a significant advance over prior art systems and methods.

DETAILED DESCRIPTION OF THE DRAWINGS

Figure 1:
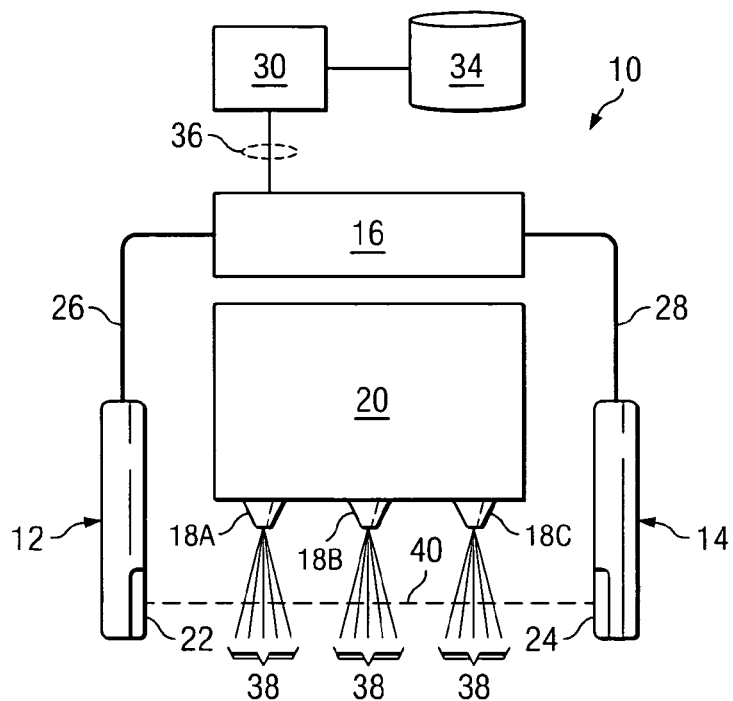
FIG. 1 is a block diagram of an exemplary system for detecting liquid flow from a nozzle in a semiconductor processing device according to one embodiment of the present invention.

FIG. 1 illustrates a block diagram of an exemplary system 10 for detecting liquid flow from nozzles 18A, 18B, and 18C (collectively, nozzles 18) in a semiconductor processing device. System 10 includes a transmitting fiber optic sensor 12, a receiving fiber optic sensor 14, and a processing module 16. Processing module 16 uses fiber optic sensors 12 and 14 to detect liquid flow from nozzles 18 of a dispense boom 20. Dispense boom 20 may be any component in a semiconductor processing device which dispenses chemicals or other liquids 38 using one or more nozzles 18. In a particular embodiment, dispense boom 20 may be in a SEZ spin processing tool, such as a SEZ01B. Dispense boom 20 may include a suckback valve which operates to prevent dripping of liquid 38.

Transmitting fiber optic sensor 12 is located on one side of nozzles 18 and transmits a light 40 below nozzles 18 to receiving fiber optic sensor 14. Fiber optic sensor 12 includes a lens 22 which is pointed in the direction of receiving fiber optic sensor 14. In a particular embodiment, transmitting fiber optic sensor 12 may be a Keyence FU-96 Fibre.

Receiving fiber optic sensor 14 is located on an opposite side of nozzles 18 from transmitting fiber optic sensor 12 and may receive light 40 transmitted by fiber optic sensor 12. Receiving fiber optic sensor 14 includes a lens 24 pointed in the direction of transmitting fiber optic sensor 12. Lens 24 may receive light 40 transmitted by fiber optic sensor 12. When nozzles 18 are not dispensing liquid 38, fiber optic sensor 14 receives a substantial amount of light 40 transmitted by fiber optic sensor 12. On the other hand, when nozzles 18 are dispensing liquid 38, liquid 38 from nozzles 18 interferes with at least some of light 40 transmitted from fiber optic sensor 12 to fiber optic sensor 14, and as a result, fiber optic sensor 14 receives less of light 40 from transmitting fiber optic sensor 12. In a particular embodiment, receiving fiber optic sensor 14 is a Keyence FU-96 Fibre.

Amp 16 generates light 40 transmitted by fiber optic sensor 12, receives light 40 from fiber optic sensor 14, and generates a signal 36 according to the amount of light 40 received by fiber optic sensor 14. Amp 16 is coupled to transmitting fiber optic sensor 12 by link 26 and is coupled to receiving fiber optic sensor 14 by link 28. In a particular embodiment, links 26 and 28 are optical fibers, and amp 16 is a Keyence FS-V21RM amp.

Amp 16 may generate a current signal 36 to indicate whether nozzles 18 are dispensing liquid 38. In a particular embodiment, amp 16 generates signal 36 at varying current levels according to the amount of light 40 received at fiber optic sensor 14 from transmitting fiber optic sensor 12. For example, in such an embodiment, amp 16 may generate signal 36 at a higher current level in response to fiber optic sensor 14 receiving a greater percentage of light 40 transmitted by the fiber optic sensor 12, and amp 16 may generate signal 36 at a lower current level in response to fiber optic sensor 14 receiving a smaller percentage of light 40 transmitted by the fiber optic sensor 12. In such an embodiment, a large current signal 36 indicates that nozzles 18 are not dispensing liquid 38 because liquid 38 is not blocking light 40 between fiber optic sensors 12 and 14, and a small current signal 36 indicates that nozzles 18 are dispensing liquid 38 which blocks light 40 between fiber optic sensors 12 and 14. In such an embodiment, a decrease in the current of signal 36 over a short period of time may indicate that nozzles 18 are dripping liquid 38.

In an alternative embodiment, amp 16 generates signal 36 at a first current level in response to determining that fiber optic sensor 14 is receiving an amount of light 40 over a defined threshold that indicates that nozzles 18 are not dispensing liquid 38, and amp 16 generates signal 36 at a second current level in response to determining that fiber optic sensor 14 is receiving an amount of light 40 below a defined threshold that indicates that nozzles 18 are dispensing liquid 38.

Amp 16 may generate a voltage signal 36 to indicate whether nozzles 18 are dispensing liquid 38. In a particular embodiment, amp 16 may generate signal 36 at varying voltage levels according to the amount of light 40 received by fiber optic sensor 14 from transmitting fiber optic sensor 12. In a particular embodiment, amp 16 generates signal 36 with a greater voltage in response to fiber optic sensor 14 receiving a greater percentage of light 40 transmitted by fiber optic sensor 12, and amp 16 generates signal 36 with a lower voltage in response to fiber optic sensor 14 receiving a smaller percentage of light 40 transmitted by fiber optic sensor 12. In such an embodiment, a large voltage signal 36 indicates that nozzles 18 are not dispensing liquid 38 because liquid 38 is not blocking light 40 between fiber optic sensors 12 and 14, and a small voltage signal 36 indicates that nozzles 18 are dispensing liquid 38 which blocks light 40 between fiber optic sensors 12 and 14. In such an embodiment, a decrease in the voltage of signal 36 over a short period of time may indicate that nozzles 18 are dripping liquid 38.

In an alternative embodiment, amp 16 generates signal 36 at a first voltage level in response to determining that fiber optic sensor 14 is receiving an amount of light 40 over a threshold that indicates that nozzles 18 are not dispensing liquid 38, and amp 16 generates signal 36 at a second voltage level in response to determining that fiber optic sensor 14 is receiving an amount of light 40 below a defined threshold that indicates that nozzles 18 are dispensing liquid 38.

Processing module 30 receives signal 36 from amp 16 and examines signal 36 to monitor the operation of dispense boom 20 and nozzles 18. In a particular embodiment, where signal 36 is a current signal, processing module 30 may determine whether nozzles 18 are dispensing liquid 38 according to the current level of signal 36. If the current level of signal 36 is above a threshold, processing module 30 determines that nozzles 18 are not dispensing liquid 38. If the current level of signal 36 is below a threshold, processing module 30 determines that nozzles 18 are dispensing liquid 38. In an alternative embodiment, where signal 36 is a voltage signal, processing module 30 may determine whether nozzles 18 are dispensing liquid 38 according to the voltage level of signal 36. If the voltage level of signal 36 is above a defined threshold, processing module 30 determines that nozzles 18 are not dispensing liquid 38. If the voltage level of signal 36 is below a defined threshold, processing module 30 determines that nozzles 18 are dispensing liquid 38. Processing module 30 analyzes signal 36 and stores data relating to the operation of nozzles 18 in a database or other memory 34.

Processing module 30 may determine whether nozzles 18 are operating properly. In response to determining that nozzles 18 are dispensing liquid 38, processing module 30 may determine whether nozzles 18 are supposed to be dispensing liquid according to a program controlling the operation of dispense boom 20 and nozzles 18. If processing module 30 determines nozzles 18 are dispensing liquid 38 but that they are not supposed to be dispensing liquid 38, processing module 30 can generate a notification of a problem. The notification may be an alarm, an e-mail, or other notice. In a particular embodiment, processing module 30 may automatically stop the operation of dispense boom 20 and nozzles 18 or stop the operation of an entire semiconductor processing device. Similarly, in response to determining that nozzles 18 are not dispensing liquid, processing module 30 may determine whether nozzles 18 are properly not dispensing liquid. If processing module 30 determines that nozzles 18 are not dispensing liquid 38 but that they should be dispensing liquid 38, processing module 30 may generate a notification or take other appropriate action. Processing module 30 may operate in conjunction with an interdiction tool, such as TIMS, which controls the operation of a semiconductor processing device. Processing module 30 may be programmed to take defined action based on certain conditions, such as determining that nozzles 18 are dispensing liquid 38 or determining that nozzles 18 are not dispensing liquid 38.

Figure 2A:
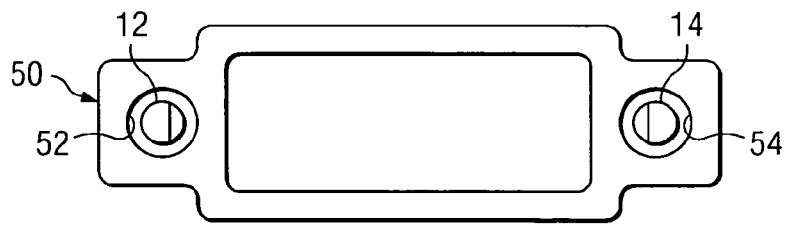
FIG. 2A is a top view of an exemplary bracket for a detection sensor.
Figure 2B:
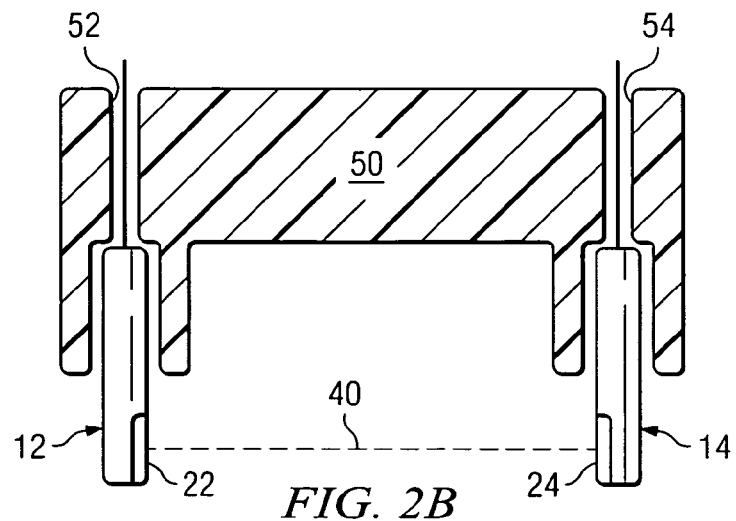
FIG. 2B is a side view of the bracket and detection sensor according to one embodiment of the present invention.

FIG. 2A is a top view of an exemplary bracket 50 for transmitting fiber optic sensor 12 and receiving fiber optic sensor 14, and FIG. 2B is a side view of bracket 50, transmitting fiber optic sensor 12, and receiving fiber optic sensor 14. Bracket 50 includes opening 52 which holds transmitting fiber optic sensor 12 and opening 54 which holds receiving fiber optic sensor 14. In a particular embodiment, transmitting fiber optic sensor 12 and receiving fiber optic sensor 14 are teflon coated and press fit into openings 52 and 54. Bracket 50 may be made of any combination of metal, plastic, composite, or other suitable material. Bracket 50 may be mounted to dispense boom 20 or any other suitable part of a semiconductor processing device. In a particular embodiment, screws, clips, or adhesive may be used to mount bracket 50 to a semiconductor processing device. As shown in the side view of FIG. 2B, lenses 22 and 24 of transmitting fiber optic sensor 12 and receiving fiber optic sensor 14 face one another so that light 40 may pass from transmitting fiber optic sensor 12 to receiving fiber optic sensor 14.

Figure 3:
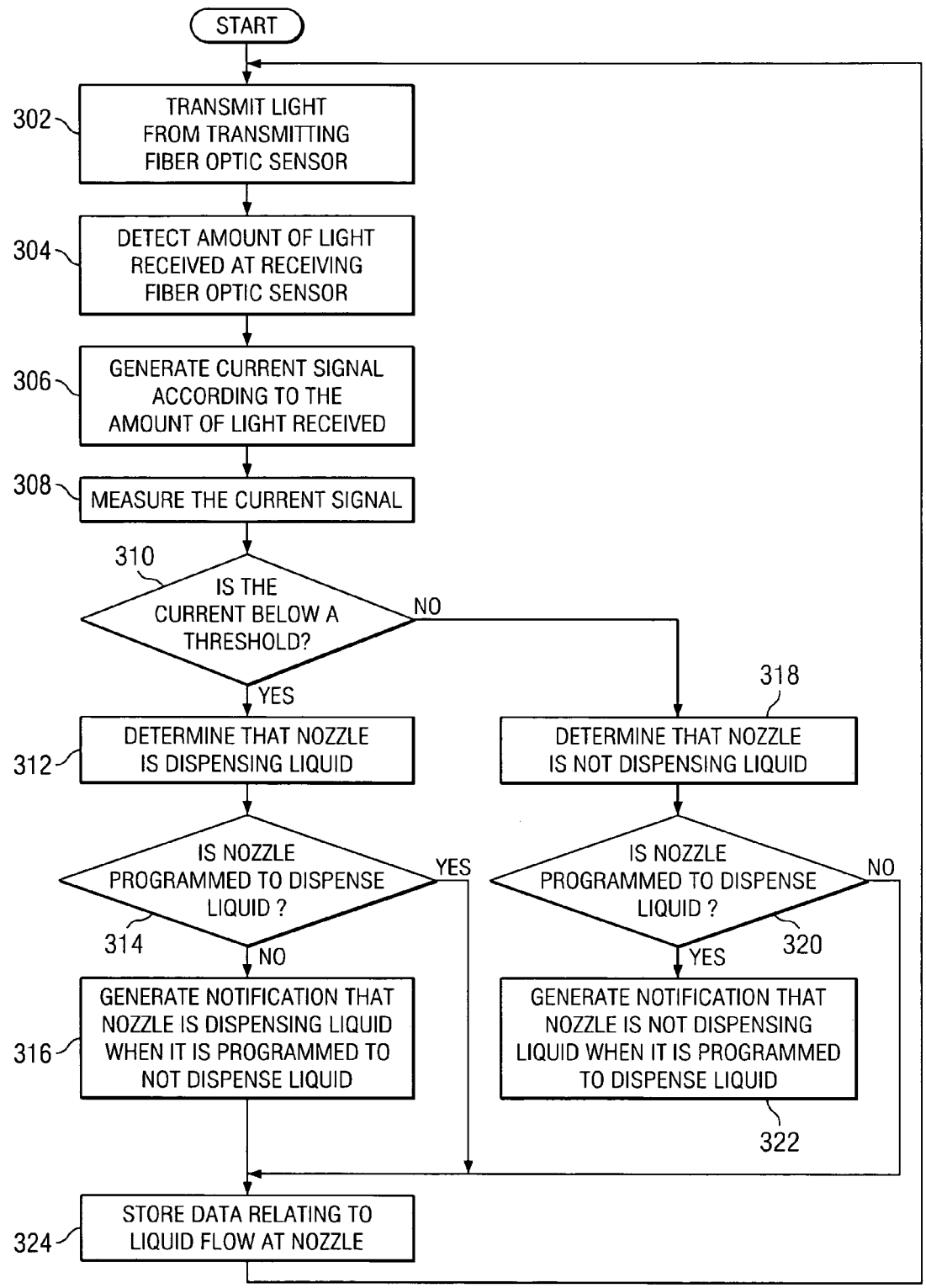
FIG. 3 is a flowchart of an exemplary method of detecting liquid flow from a nozzle in a semiconductor processing device, which uses a current signal.

FIG. 3 is a flowchart of an exemplary method of detecting liquid flow from nozzles 18 in a semiconductor processing device, which uses a current signal 36. The method begins at step 302, where transmitting fiber optic sensor 12 transmits light 40 to receiving fiber optic sensor 14. As discussed above with reference to FIG. 1, transmitting fiber optic sensor 12 and receiving fiber optic sensor 14 are located on opposite sides of one or more nozzles 18. At step 304, amp 16 detects an amount of light 40 received at fiber optic sensor 14. At step 306, amp 16 generates current signal 36 according to the amount of light 40 received at fiber optic sensor 14. In a particular embodiment, amp 16 generates signal 36 with a greater amount of current in response to fiber optic sensor 14 receiving a greater amount of light 40. In an alternative embodiment, amp 16 generates signal 36 with a first current level in response to determining that fiber optic sensor 14 received an amount of light 40 above a defined threshold and generates signal 36 at a second current level in response to determining that fiber optic sensor 14 received an amount of light 40 below a defined threshold.

Processing module 30 measures the current of signal 36 at step 308 and determines whether the current is below a threshold at step 310. If the current is below the threshold, processing module 30 determines that nozzles 18 are dispensing liquid 38 at step 312, and if the nozzle is not programmed to dispense liquid 38 at step 314, processing module 30 generates a notification that nozzles 18 are dispensing liquid 38 when programmed not to dispense liquid 38 at step 316. If the current of signal 36 is not below the threshold at step 310, processing module 30 determines that nozzles 18 are not dispensing liquid 38 at step 318, and if the nozzle is programmed to dispense liquid 38 at step 320, processing module 30 generates a notification that nozzles 18 are not dispensing liquid 38 when programmed to dispense liquid 38 at step 322. Processing module 30 stores data relating to liquid flow at nozzles 18 in a database or other memory 34 at step 324, and the method returns to step 302.

Figure 4:
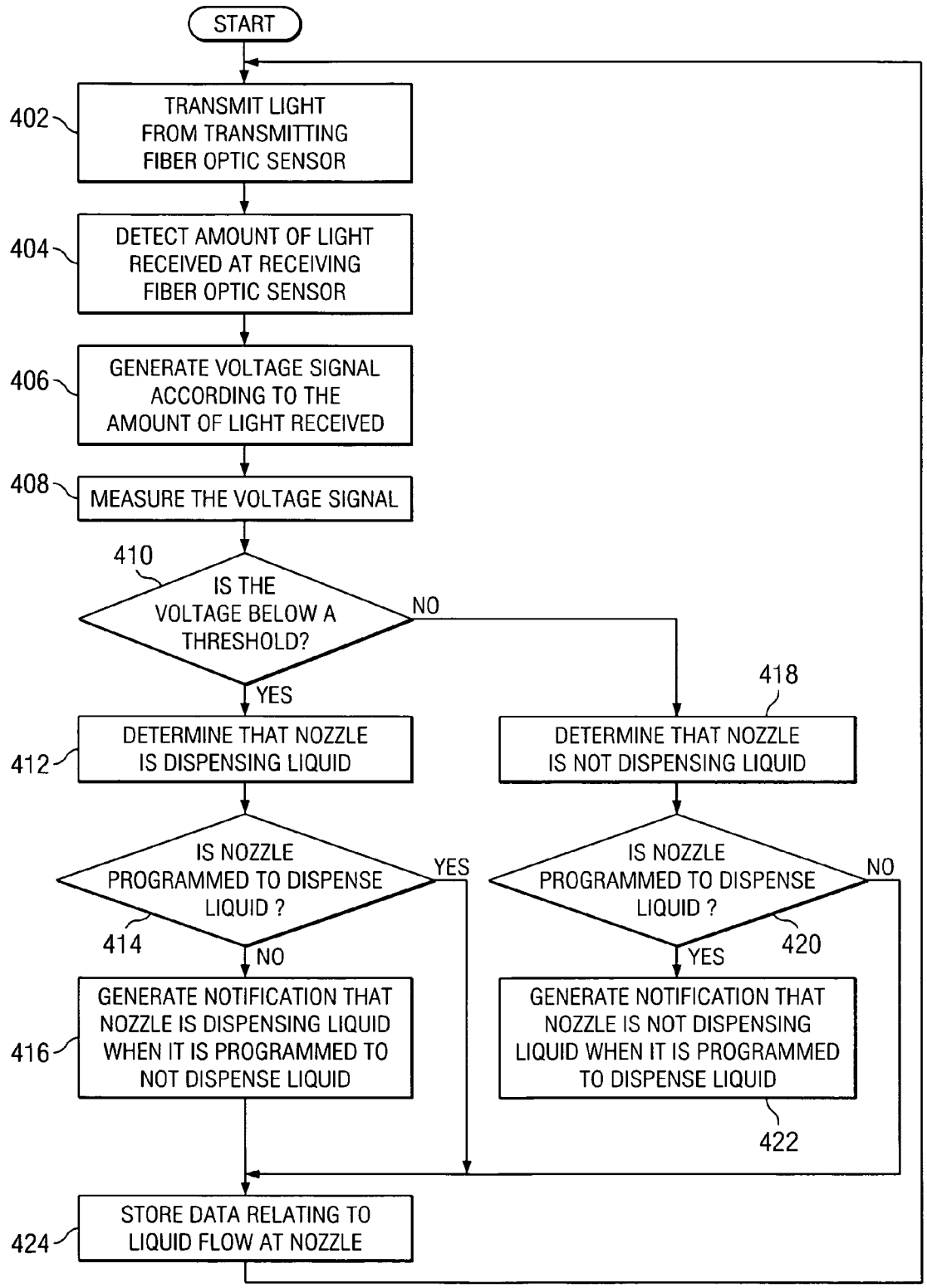
FIG. 4 is a flowchart for a method for detecting liquid flow from a nozzle in a semiconductor processing device, which uses a voltage signal.

FIG. 4 is an exemplary flowchart for a method of detecting liquid flow from nozzle 18 in a semiconductor processing device, where signal 36 is a voltage signal. The method begins at step 402, where transmitting fiber optic sensor 12 transmits light 40 to receiving fiber optic sensor 14. As discussed above with reference to FIG. 1, transmitting fiber optic sensor 12 and receiving fiber optic sensor 14 are located on opposite sides of at least one nozzle 18.

At step 404, amp 16 detects an amount of light 40 received at fiber optic sensor 14. At step 406, amp 16 generates signal 36 at a voltage level according to the amount of light 40 received at fiber optic sensor 14. In a particular embodiment, amp 16 generates signal 36 with a greater amount of voltage in response to fiber optic sensor 14 receiving a greater amount of light 40. In an alternative embodiment, amp 16 generates signal 36 with a first voltage level in response to determining that fiber optic sensor 14 received an amount of light 40 above a defined threshold and generates signal 36 at a second voltage level in response to determining that fiber optic sensor 14 received an amount of light 40 below a defined threshold.

Processing module 30 measures the voltage level of signal 36 at step 408 and determines whether the measured voltage is below a defined threshold at step 410. If the measured voltage is below the defined threshold, processing module 30 determines that nozzle 18 is dispensing liquid 38 at step 412, and if nozzle 18 is not programmed to dispense liquid 38 at step 414, processing module 30 generates a notification that nozzle 18 is dispensing liquid 38 when it is programmed to not dispense liquid 38 at step 416. If processing module 30 determines that the voltage level of signal 36 is not below the defined threshold at step 410, processing module 30 determines that nozzle 18 is not dispensing liquid 38 at step 418, and if nozzle 18 is programmed to dispense liquid 38 at step 420, processing module 30 generates a notification that the nozzle 18 is not dispensing liquid 38 when it is programmed to dispense liquid 38 at step 422. At step 424, processing module 30 stores data relating to liquid flow at nozzle 18 in memory 34, and the method continues at step 402.

In the particular embodiment of the invention described above, amp 16 generates a lower current or voltage signal 36 when liquid 38 from nozzles 18 is blocking light 40 between fiber optic sensors 12 and 14, and amp 16 generates a higher current or voltage signal 36 when liquid 38 from nozzles 18 is not blocking light 40 between fiber optic sensors 12 and 14. However, in an alternative embodiment, these relationships may be reversed. Amp 16 may generates a higher current or voltage signal 36 when liquid 38 from nozzles 18 is blocking light 40 between fiber optic sensors 12 and 14, and amp 16 may generate a lower current or voltage signal 36 when liquid 38 from nozzles 18 is not blocking light 40 between fiber optic sensors 12 and 14. In such an embodiment, processing module 30 may determine that nozzles 18 are dispensing liquid 38 when it detects a high current or voltage signal 36, and processing module 30 may determine that nozzles 18 are not dispensing liquid 38 when it detects a low current or voltage signal 36.

Although an embodiment of the invention and its advantages are described in detail, a person skilled in the art could make various alterations, additions, and omissions without departing from the spirit and scope of the present invention as defined by the appended claims.

What is claimed is:

1. A system for detecting liquid flow from a nozzle in a semiconductor processing device, comprising:
    a first fiber optic sensor and a second fiber optic sensor located on opposite sides of at least one nozzle, the first fiber optic sensor operable to transmit light, the second fiber optic sensor operable to receive more of the light when the nozzle is not dispensing liquid than when the nozzle is dispensing liquid; and
    an amp coupled to the first fiber optic sensor and second fiber optic sensor and operable to indicate whether the nozzle is dispensing liquid according to an amount of the light received at the second fiber optic sensor.

2. The system of claim 1, wherein the amp is further operable to generate a first current if the amount of the light received at the second fiber optic sensor indicates that the nozzle dispensing the liquid and operable to generate a second current if the amount of the light receive at the second fiber optic sensor indicates that the nozzle is not dispensing the liquid.

3. The system of claim 1, wherein the amp is operable to generate a current according to the amount of the light received by the second fiber optic sensor, the amp operable to generate more current in response to the second fiber optic sensor receiving a greater percentage of the light transmitted from the first fiber optic sensor.

4. The system of claim 3, wherein a decrease in the current over a short period of time may indicate that the nozzle is dripping the liquid.

5. The system of claim 1, wherein the amp is further operable to generate a first voltage if the amount of the light received at the second fiber optic sensor indicates that the nozzle dispensing liquid and operable to generate a second voltage if the amount of the light received at the second fiber optic sensor indicates that the nozzle is not dispensing liquid.

6. The system of claim 1, wherein the amp is further operable to generate a voltage according to the amount of the light received by the second fiber optic sensor, the amp operable to generate more voltage in response to the second fiber optic sensor receiving a greater percentage of the light transmitted from the first fiber optic sensor.

7. The system of claim 6, wherein a decrease in the voltage over a short period of time may indicate that the nozzle is dripping the liquid.

8. The system of claim 1, further comprising a processing module operable to determine whether the nozzle is dispensing the liquid when the nozzle is programmed not to dispense the liquid and to generate a notification in response to determining that the nozzle is dispensing the liquid when the nozzle is programmed not to dispense the liquid.

9. The system of claim 1, further comprising a processing module operable to determine whether the nozzle is not dispensing the liquid when the nozzle is programmed to dispense the liquid and to generate a notification in response to determining that the nozzle is dispensing the liquid when the nozzle is programmed not to dispense the liquid.

10. The system of claim 1, further comprising a processing module operable to determine whether the nozzle is dispensing the liquid and to store data indicating whether the nozzle is dispensing the liquid.

* * * * *